(12) United States Patent
Flynn et al.

(10) Patent No.: US 7,988,877 B2
(45) Date of Patent: Aug. 2, 2011

(54) METHODS OF MAKING FLUORINATED ETHERS, FLUORINATED ETHERS, AND USES THEREOF

(75) Inventors: Richard M. Flynn, Mahtomedi, MN (US); Michael J. Bulinski, Houlton, WI (US); Michael G. Costello, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 198 days.

(21) Appl. No.: 12/263,661

(22) Filed: Nov. 3, 2008

(65) Prior Publication Data

US 2010/0108934 A1 May 6, 2010

(51) Int. Cl.
*A62D 1/00* (2006.01)
*C07C 43/00* (2006.01)
*C07C 43/12* (2006.01)
(52) U.S. Cl. ............. 252/2; 568/677; 568/681; 568/683
(58) Field of Classification Search .................. 568/677, 568/681; 252/2
See application file for complete search history.

(56) References Cited

U.S. PATENT DOCUMENTS

| | | |
|---|---|---|
| 3,903,012 A | 9/1975 | Brandreth |
| 4,169,807 A | 10/1979 | Zuber |
| 5,089,152 A | 2/1992 | Flynn et al. |
| 5,125,089 A | 6/1992 | McCambridge |
| 5,125,978 A | 6/1992 | Flynn et al. |
| 5,182,342 A | 1/1993 | Feiring et al. |
| 5,210,106 A | 5/1993 | Dams et al. |
| 5,474,657 A | 12/1995 | Hansen |
| 5,539,008 A | 7/1996 | Dams et al. |
| 5,718,293 A | 2/1998 | Flynn et al. |
| 5,839,311 A | 11/1998 | Grenfell et al. |
| 5,925,611 A | 7/1999 | Flynn et al. |
| 6,023,002 A | 2/2000 | Behr et al. |
| 6,046,368 A | 4/2000 | Lamanna et al. |
| 6,080,448 A | 6/2000 | Leiner et al. |
| 6,399,729 B1 | 6/2002 | Farnham et al. |
| 6,759,374 B2 | 7/2004 | Milbrath et al. |
| 7,128,133 B2 | 10/2006 | Costello et al. |
| 7,390,427 B2 | 6/2008 | Costello et al. |
| 2007/0051916 A1 | 3/2007 | Flynn et al. |
| 2007/0054186 A1 | 3/2007 | Costello et al. |
| 2008/0139683 A1 | 6/2008 | Flynn et al. |

FOREIGN PATENT DOCUMENTS

RU 2 312 097 C1 12/2007

OTHER PUBLICATIONS

"Organic Chemistry" (Brown and Foote, 2nd Edition, 1998, Saunders Publishing, pp. 291-292).*

Rakhimov et al., "Synthesis of Di(polyfluoroalkyl) Ethers", Russian Journal of Applied Chemistry, vol. 77, No. 9, 2004, pp. 1561-1563.
Research Disclosure, "Hydrofluoroethers as Fluoromonomer Reaction Media", No. 405, Jan. 1998, pp. 81-82.
Rakhimov et al., "Reaction of Polyfluorinated Alcohols with Thionyl Chloride", Russian Journal of Organic Chemistry, vol. 35, No. 3, 1999, pp. 794-795.
L. Z. Gandel'sman et al., "1,1-Dihydropolyfluoroalkylation of N-Alkylanilines," Journal of Organic Chemistry of the USSR, vol. 14, No. 4, Part 2, Apr. 1978, 4 pages.
Johncock, "Sulphur-Oxygen Versus Carbon-Oxygen Scission in Trifluoromethanesulphonates", Journal of Fluorine Chemistry, vol. 4, 1974, pp. 25-33.
Burdon et al., "Trifluoromethanesulphonate Esters and Their Alkylating Properties", Tetrahedron, vol. 21, 1965, pp. 1-4.
"Hydrofluoroacetal Compounds and Processes for their Preparation and Use", U.S. Appl. No. 12/164,369, filed Jun. 30, 2008.
Hals, Lyle J., et al., "Fluorine Compounds, Organic: Fluoro Ethers and Amines", Database CA [Online], XP002581100 retrieved from STN Database accession No. 65:72826, Chemical Abstracts Service, Columbus, Ohio, US, 1966, abstract.
Henne, A., L., et al., "Fluorinated Ethers", Journal of the American Chemical Society, 1950, vol. 72, pp. 4378-4380.
Beilstein Database [Online], Beilstein Institute for Organic Chemistry, Database Accession No. BRN 1824673 Abstract & Journal of Organic Chemistry, Frankfurt-Main, DE, 1960, vol. 25, pp. 1682-1683.
PCT International Searching Authority, "Invitation to Pay Additional Fees and, Where Applicable, Protest Fee", International Application Number: PCT/US2009/060326, Applicant's Reference: 64680WO003, May 5, 2010.
PCT Written Opinion of the International Searching Authority, PCT/US2009/060326, mailed Dec. 27, 2010, 11 pages.
PCT International Search Report, PCT/US2009/060326, mailed Dec. 27, 2010, 5 pages.

* cited by examiner

*Primary Examiner* — Mark Eashoo
*Assistant Examiner* — Peter F Godenschwager
(74) *Attorney, Agent, or Firm* — Bradford B. Wright

(57) ABSTRACT

A method of making a fluorinated ether includes combining, in a polar aprotic solvent: a fluorinated alcohol represented by the formula $X-R_f^1CH_2OH$, and a fluorinated sulfonate ester represented by the formula $R_f^2CH_2OS(=O)_2R_f^3$, and base; and obtaining a fluorinated ether represented by the formula $Y-R_f^1CH_2OCH_2R_f^2$—Y. $R_f^1$ is selected from perfluorinated $C_1$-$C_{10}$ alkylene groups having from 1 to 10 carbon atoms and partially fluorinated $C_1$-$C_{10}$ alkylene groups, and derivatives thereof having catenated heteroatom(s). X represents H, F, or an $HOCH_2$— group. $R_f^2$ is selected from perfluorinated $C_1$-$C_{10}$ alkyl groups and partially fluorinated $C_1$-$C_{10}$ alkyl groups, and derivatives thereof having catenated heteroatom(s). $R_f^3$ is a $C_1$-$C_4$ alkyl group. Y represents H, F, or an $R_f^2CH_2OCH_2$— group. A variant method, useful for preparing symmetric fluorinated ethers, is also disclosed. The present disclosure also provides fluorinated ethers preparable according to the methods. Use of fluorinated ethers in various applications is also disclosed.

5 Claims, No Drawings

METHODS OF MAKING FLUORINATED ETHERS, FLUORINATED ETHERS, AND USES THEREOF

TECHNICAL FIELD

The present disclosure broadly relates to fluorinated ethers, methods for making fluorinated ethers, and uses thereof.

BACKGROUND

Various fluorinated ethers are known. The term hydrofluoroether, as used in the art, commonly refers to those ethers having partial substitution of hydrogen atoms by fluorine atoms. Some hydrofluoroethers are commercially available. Examples include those hydrofluoroethers available under the trade designations 3M NOVEC ENGINEERED FLUID 7000, 7100, 7200, 7300, 7500, and 7600 from 3M Company of Saint Paul, Minn.

SUMMARY

In one aspect, the present disclosure provides a method of making a fluorinated ether, the method comprising:
combining in a polar aprotic solvent:
a fluorinated alcohol represented by the formula $$X-R_f^1-CH_2OH$$

wherein
$R_f^1$ is selected from the group consisting of perfluorinated alkylene groups having from 1 to 10 carbon atoms, partially fluorinated alkylene groups having from 1 to 10 carbon atoms, and derivatives thereof wherein one or more carbon atoms are replaced by catenated heteroatoms, wherein if $R_f^1$ contains at least two carbon atoms, then $R_f^1$ contains at most two hydrogen atoms; and
X represents H, F, or an $HOCH_2-$ group;
a fluorinated sulfonate ester represented by the formula $$R_f^2CH_2OS(=O)_2R_f^3$$

wherein
$R_f^2$ is selected from the group consisting of perfluorinated alkyl groups having from 1 to 10 carbon atoms and partially fluorinated alkyl groups having from 1 to 10 carbon atoms, and derivatives thereof wherein one or more carbon atoms are replaced by catenated heteroatoms, and wherein if $R_f^2$ contains at least two carbon atoms then $R_f^2$ contains at most three hydrogen atoms; and $R_f^3$ is selected from the group consisting of perfluorinated alkyl groups having from 1 to 4 carbon atoms; and
base; and
obtaining at least one fluorinated ether represented by the formula $$Y-R_f^1-CH_2OCH_2R_f^2$$

wherein Y represents H, F, or an $R_f^2CH_2OCH_2-$ group.

In another aspect, the present disclosure provides a fluorinated ether represented by the formula $$Y-R_f^1-CH_2OCH_2R_f^2$$

wherein
$R_f^1$ is selected from the group consisting of perfluorinated alkylene groups having from 1 to 10 carbon atoms, partially fluorinated alkylene groups having from 1 to 10 carbon atoms, and derivatives thereof wherein one or more carbon atoms are replaced by catenated heteroatoms, wherein if $R_f^1$ contains at least two carbon atoms, then $R_f^1$ contains at most two hydrogen atoms; and
Y represents H, F, or an $R_f^2CH_2OCH_2-$ group, wherein $R_f^2$ is selected from the group consisting of perfluorinated alkyl groups having from 1 to 10 carbon atoms and partially fluorinated alkyl groups having from 1 to 10 carbon atoms, and derivatives thereof wherein one or more carbon atoms are replaced by catenated heteroatoms, wherein if $R_f^2$ contains at least two carbon atoms, then $R_f^2$ contains at most three hydrogen atoms; and
wherein
if Y is F and $R_f^1$ and $R_f^2$ are both perfluorinated groups, then at least one of $R_f^1$ or $R_f^2$ has at least 3 carbon atoms, and
if $Y-R_f^1-$ contains an $HCF_2-$ group then $R_f^2$ does not contain a $-CF_2H$ group.

In yet another aspect, the present disclosure provides a method of making a fluorinated ether, the method comprising:
combining in a polar aprotic solvent:
a fluorinated alcohol represented by the formula $$Z-R_f^1-CH_2OH$$

wherein:
Z represents H or F;
$R_f^1$ is selected from the group consisting of perfluorinated alkylene groups having from 1 to 10 carbon atoms and partially fluorinated alkylene groups having from 1 to 10 carbon atoms, and derivatives thereof wherein one or more carbon atoms are replaced by catenated heteroatoms, wherein if $R_f^1$ contains at least two carbon atoms, then $R_f^1$ contains at most two hydrogen atoms; and
a sulfonyl fluoride represented by the formula $$R_f^3S(=O)_2F$$

wherein $R_f^3$ is selected from the group consisting of perfluorinated alkyl groups having from 1 to 4 carbon atoms; and
base; and
obtaining a fluorinated ether represented by the formula $$Z-R_f^1-CH_2OCH_2-R_f^1-Z.$$

In some embodiments, at least one of $R_f^1$ or $R_f^2$ contains a secondary carbon atom having one hydrogen atom and one fluorine atom bonded thereto. In some embodiments, at least one of $R_f^1$ or $R_f^2$ has from 3 to 8 carbon atoms. In some embodiments, at least one of $R_f^1$ or $R_f^2$ has from 3 to 5 carbon atoms.

Compounds according to the present disclosure are useful, for example, in cleaning solvents, in fire extinguishing compositions, in blowing agents used in the manufacture of foamed plastics, as coating solvents, as polymerization media, for drying substrates, and in working fluids for cutting or abrading processes.

Accordingly, in yet another aspect, the present disclosure provides a method of using a fluorinated ether, the method comprising cleaning a workpiece with a composition comprising a fluorinated ether represented by the formula $$Y-R_f^1-CH_2OCH_2R_f^2$$

wherein
$R_f^1$ is selected from the group consisting of perfluorinated alkylene groups having from 1 to 10 carbon atoms, partially fluorinated alkylene groups having from 1 to 10 carbon atoms, and derivatives thereof wherein one or more carbon atoms are replaced by catenated heteroatoms, wherein if $R_f^1$ contains at least two carbon atoms, then $R_f^1$ contains at most two hydrogen atoms; and Y represents H, F, or an $R_f^2CH_2OCH_2$— group, wherein $R_f^2$ is selected from the group consisting of perfluorinated alkyl groups having from 1 to 10 carbon atoms and partially fluorinated alkyl groups having from 1 to 10 carbon atoms, and derivatives thereof wherein one or more carbon atoms are replaced by catenated heteroatoms, wherein if $R_f^2$ contains at least two carbon atoms, then $R_f^2$ contains at most three hydrogen atoms.

As used herein:

"alkyl group" refers to a monovalent non-aromatic hydrocarbyl group that may be linear, branched, cyclic, or any combination thereof;

"catenated heteroatom" refers to a nitrogen atom or an oxygen atom that is bonded to carbon atoms in a carbon chain so as to form a carbon-heteroatom-carbon chain;

"F" represents a fluorine atom;

"fluorinated alkyl" means the at least one H atom of the alkyl group has been replaced by fluorine;

"H" represents a hydrogen atom;

"nonaflate" refers to perfluoro-n-butanesulfonate;

"perfluorinated" means that all H atoms that are bonded to carbon are replaced by F atoms;

"triflate" refers to trifluoromethanesulfonate;

"polar aprotic solvent" refers to a solvent that is substantially free of —OH and —NH— groups (i.e., does not contain —OH and —NH— groups in more than adventitious amounts); and "X", "Y", and "Z" represent variable chemical groups.

DETAILED DESCRIPTION

Methods of making fluorinated ethers according to the present disclosure are carried out in polar aprotic solvents. Many such solvents are known and used in the chemical arts. Examples include tetrahydrofuran (THF), acetone, dimethyl sulfoxide (DMSO), hexamethylphosphoramide (HMPA), N,N-dimethylacetamide (DMA), diethylene glycol dimethyl ether, and N,N-dimethylformamide. The polar aprotic solvent may contain minor amounts of nonpolar aprotic compounds, provided sufficient polarity of the mixed solvent is retained. In some embodiments acetone is specifically desirable.

A first method involves mixing a fluorinated alcohol with a fluorinated sulfonate ester, and base in the polar aprotic solvent under conditions such that a fluorinated ether is formed.

The fluorinated alcohol may be represented by the formula

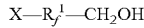

X—$R_f^1$—$CH_2OH$ wherein:

$R_f^1$ is selected from the group consisting of perfluorinated alkylene groups having from 1 to 10 carbon atoms and partially fluorinated alkylene groups having from 1 to 10 carbon atoms, and derivatives thereof wherein one or more carbon atoms are replaced by catenated heteroatoms, wherein if $R_f^1$ contains at least two carbon atoms, then $R_f^1$ contains at most two hydrogen atoms.

Exemplary divalent groups $R_f^1$ include: perfluorinated alkylene groups such as, for example, perfluoromethylene, perfluoroethylene (i.e., perfluoroethane-1,2-diyl), perfluoropropane-1,3-diyl, perfluoropropane-1,2-diyl, perfluoro(2-methylpropane-1,3-diyl), perfluoropentane-1,5-diyl, perfluorohexane-1,6-diyl, perfluorocyclohexane-1,4-diyl, and perfluorooctane-1,8-diyl; and partially fluorinated alkyl groups such as, for example, fluoromethylene, 1,1,2,2-tetrafluoroethylene, 1,1,2,3,3-pentafluoropropane-1,3-diyl, and 1,1,2,2,3,3,4,4-octafluorobutane-1,4-diyl. Exemplary derivatives of perfluorinated and partially fluorinated alkyl groups include fluorinated alkoxyalkyl groups such as —$CF_2CF_2OCF_2CF_2$—, —$CF_2CF_2CF_2OCF_2CF_2$—, —$CF_2OCF_2CF_2$—; —$CF_2CF_2CF_2OCF(CF_3)$—; —$CF_2CF_2CF_2OCF(CF_3)CF_2OCF(CF_3)$—; —$CF_2OC_3F_6OCF(CF_3)$—; —$CF_2CF_2CF_2OCF(CF_3)$—, —$CH_2OC_3F_6$—, —$CF_2OC_3F_6$—, —$CF_2CF_2CF_2OCFHCF_2$—, —$CF_2CF_2CF_2OCF(CF_3)CF_2OCFHCF_2$—, —$CF_2OC_3F_6OCFHCF_2$—, —$CF_2O(CF_2CF_2O)_xCF_2$— (wherein x is an integer greater than or equal to 1), —$CF_2CF_2N(CF_2CF_3)CF_2CF_2$—, —$CF_2(CF_3)NC_2F_4$—, —$C_3F_6(C_3F_7)NC_2F_4$—, and —$CF_2CF_2CF_2N(CF_3)CF_2$—.

X represents H, F, or an $HOCH_2$— group. In some embodiments, the fluorinated alcohol may be multifunctional, which results in a corresponding polyether. Examples of multifunctional fluorinated alcohols include $HOCH_2C_2F_4CH_2OH$, $HOCH_2C_3F_6CH_2OH$, $HOCH_2C_4F_8CH_2OH$, $HOCH_2(CF_2CF_2O)_nCH_2OH$ wherein n is a positive integer, and $HOCH_2CF_2O(C_2F_4O)j(CF_2O)_kCF_2CH_2OH$ wherein j and k represent integers in a range of from 1 to 50. In such cases X represents $HOCH_2$—.

The fluorinated sulfonate ester is represented by the formula $R_f^2CH_2OS(=O)_2R_f^3$ wherein $R_f^2$ is selected from the group consisting of perfluorinated alkyl groups having from 1 to 10 carbon atoms and partially fluorinated alkyl groups having from 1 to 10 carbon atoms, and derivatives thereof wherein one or more carbon atoms are replaced by catenated heteroatoms. If $R_f^2$ contains at least two carbon atoms then $R_f^2$ contains at most three hydrogen atoms. $R_f^3$ is chosen from the group consisting of perfluorinated alkyl groups having from 1 to 4 carbon atoms; and Exemplary groups $R_f^2$ include perfluoromethyl, perfluoroethyl, perfluoropropyl, perfluoroisopropyl, perfluorobutyl, perfluoroisobutyl, perfluoropentyl, perfluorohexyl, perfluorocyclohexyl, and perfluorooctyl; and partially fluorinated alkyl groups such as, for example, 1,1,2,2-tetrafluoroethyl, 1,1,2,3,3,3-hexafluoropropyl, and 1,1,2,2,3,3,4,4-octafluorobutyl, and derivatives of perfluorinated and partially fluorinated alkyl groups such as $HCF_2CF_2OCF_2CF_2$—, $CF_3CF_2OCF_2CF_2$—, $HCF_2CF_2CF_2OCF_2CF_2$—, $CF_3CF_2CF_2OCF_2$—, $CF_3OCF_2CF_2$—; $C_3F_7OCF(CF_3)$—; $C_3F_7OCF(CF_3)CF_2OCF(CF_3)$—; $CF_3OC_3F_6OCF(CF_3)$—; $C_4F_9OCF(CF_3)$—, $CH_3OC_3F_6$—, $C_3F_7OCFHCF_2$—, $C_3F_7OCF(CF_3)CF_2OCFHCF_2$—, $CF_3OC_3F_6OCFHCF_2$—, $CF_3O(CF_2CF_2O)yCF_2$— (wherein y is an integer greater than or equal to 1), $CF_3CF_2N(CF_2CF_3)CF_2CF_2$—, $(CF_3)_2NC_2F_4$—, $(C_3F_7)_2NC_2F_4$—, and $CF_3CF_2CF_2N(CF_3)CF_2$—.

Y represents H, F, or an $R_f^2CH_2OCH_2$— group, wherein $R_f^2$ is as described above.

Typically, the fluorinated alcohol and the fluorinated sulfonate ester are combined in approximately the same equivalent amounts (a 1:1 equivalent ratio), although other ratios may be used; for example, a molar ratio in a range of from 0.8 to 1.2.

Useful bases include organic and inorganic bases. Exemplary bases include alkali metal carbonates (optionally in combination with a tetraalkylammonium halide), tertiary amines, sodium hydride, and combinations thereof.

The combined components are placed in a pressure vessel under conditions that cause reaction of the components and formation of the corresponding fluorinated ether, although in some cases the reactions can be carried out in glass vessels at ambient pressure. Typical conditions include stirring and heating, although in some cases one or neither may be desirable. After sufficient time has elapsed the mixture is typically returned to ambient temperature (if heated), then the fluorinated ether is obtained by workup and purification; for example, as described in the Examples.

In a second method, useful for preparing symmetrical fluorinated ethers according to the present disclosure, the fluorinated alcohol (that is, a partially fluorinated alcohol) as described above is combined with a perfluoroalkanesulfonyl fluoride having from 1 to 4 carbon atoms, in a polar aprotic solvent. Typically mild heating is applied to facilitate reaction in a timely manner.

Methods of preparing fluorinated ethers according to the present disclosure are also useful, for example, for preparing fluorinated ethers represented by the formula

$$Z-R_f^1-CH_2OCH_2-R_f^1-Z.$$

wherein $R_f^1$ is as previously defined, and Z represents H or F (i.e., both Z groups are H or both Z groups represent F.

Fluorinated ethers according to the present disclosure and compositions (typically liquid) comprising them, may be used in various applications where chlorofluorocarbons (CFCs) have been used. For example, the fluorinated ethers can be used in solvent compositions for precision or metal cleaning of electronic articles such as disks or circuit boards; as cell size regulators in making foam insulation (for example, polyurethane, phenolic, or thermoplastic foams); in chemical fire extinguishing compositions in streaming applications; in carrier fluids or solvents for document preservation materials; as and in lubricants; in inert compositions for carrying out polymerization reactions; in displacement drying compositions for removing water, such as from jewelry or metal parts; in resist developer compositions in conventional circuit manufacturing techniques including chlorine-type developing agents; and in stripper compositions for photoresists when used with, for example, a chlorohydrocarbon such as cis-or trans-dichloroethene or trichloroethylene. In such applications, diastereomeric mixtures of these fluorinated ethers can typically be used without any further resolution into enantiomeric forms, however, in some embodiments a single enantiomer may be used.

The fluorinated ethers can be used alone or in admixture with each other or with other commonly-used solvents (for example, alcohols, ethers, alkanes, alkenes, perfluorocarbons, perfluorinated tertiary amines, perfluorinated ethers, cycloalkanes, esters, ketones, aromatics, siloxanes, hydrochlorocarbons, hydrofluorocarbons, and mixtures thereof). Such co-solvents can be typically chosen to modify or enhance the properties of a composition for a particular use and can be utilized in ratios (of co-solvent(s) to fluorinated ether(s)) such that the resulting composition has essentially no flash point. If desired, the fluorinated ethers can be used in combination with other compounds that are very similar in properties relative to a particular use (for example, other fluorinated ethers).

Minor amounts of optional components can be added to the fluorinated ethers to impart particular desired properties for particular uses. Useful compositions can comprise conventional additives such as, for example, surfactants, coloring agents, stabilizers, anti-oxidants, flame retardants, and mixtures thereof.

Fluorinated ethers according to the present disclosure, whether alone or in compositions containing them, can typically be used as solvents for cleaning and drying applications such as, for example, those described in U.S. Pat. No. 5,125, 089 (Flynn et al.), U.S. Pat. No. 3,903,012 (Brandreth), U.S. Pat. No. 4,169,807 (Zuber), and U.S. Pat. No. 5,925,611 (Flynn et al.). Both organic and inorganic substrates can be cleaned by contacting them with a composition comprising at least one fluorinated ether according to the present disclosure. Most contaminants can be removed, including hydrocarbon contaminants, fluorocarbon contaminants, particulates, and water.

In using fluorinated ethers according to the present disclosure for the drying of or displacing water from the surface of articles (such as circuit boards), a process of drying or water displacement generally as described in U.S. Pat. No. 5,125, 978 (Flynn et al.) can be used. That process comprises contacting the surface of an article with a liquid composition comprising at least one fluorinated ether according to the present disclosure, typically in admixture with a non-ionic fluoroaliphatic surface active agent. The wet article is immersed in the liquid composition and agitated therein, the displaced water is separated from the liquid composition, and the resulting water-free article is removed from the liquid composition.

If using fluorinated ethers according to the present disclosure as cell size regulators in making plastic foam (such as foamed polyurethane), the process reactants and reaction conditions described in, for example, U.S. Pat. No. 5,210,106 (Dams et al.) and U.S. Pat. No. 5,539,008 (Dams et al.) can be used. One such process comprises vaporizing a blowing agent mixture in the presence of at least one foamable polymer or the precursors of at least one foamable polymer, the blowing agent mixture comprising at least one fluorinated ether according to the present disclosure.

If using the fluorinated ethers according to the present disclosure as deposition solvents in coating applications or in document preservation applications, the processes generally described in U.S. Pat. No. 5,925,611 (Flynn et al.) and U.S. Pat. No. 6,080,448 (Leiner et al.) can be used. Such processes for depositing a coating on a substrate (for example, magnetic recording media or cellulose-based materials) comprise applying, to at least a portion of at least one surface of the substrate, a composition comprising (a) a solvent composition comprising at least one fluorinated ether according to the present disclosure; and (b) at least one coating material that is soluble or dispersible in the solvent composition. Exemplary coating materials that can be deposited by the process include pigments, lubricants, stabilizers, adhesives, anti-oxidants, dyes, polymers, pharmaceuticals, release agents, inorganic oxides, document preservation materials (for example, alkaline materials used in the deacidification of paper), and combinations thereof.

If using fluorinated ethers according to the present disclosure as fire extinguishing and prevention agents, the processes generally described in U.S. Pat. No. 5,718,293 (Flynn et al.) may be used. Such processes for the extinction of fires comprise applying or introducing to a fire a composition comprising at least one fluorinated ether according to the present disclosure. Fluorinated ethers according to the present disclosure may be used alone or in combination with other fire extinguishing or prevention agents.

If using the fluorinated ethers according to the present disclosure in cutting or abrasive working operations, the processes generally described in U.S. Pat. No. 6,759,374 (Milbrath et al.) can be used. Such a process for metal, cermet, or composite working comprises applying a working fluid to the metal, cermet, or composite workpiece and tool, the working fluid comprising at least one fluorinated ether according to the present disclosure and at least one lubricious additive. The working fluid may further comprise one or more additives (for example, corrosion inhibitors, antioxidants, defoamers, dyes, bactericides, freezing point depressants, metal deactivators, co-solvents, and the like, and mixtures thereof).

If using fluorinated ethers according to the present disclosure as polymerization media or as chain transfer agents, the processes generally described in *Research Disclosure* (January 1998, Number 405), 40576, page 81 and in U.S. Pat. No. 5,182,342 (Feiring et al.) and U.S. Pat. No. 6,399,729 (Farnham et al.) may be used. Such processes comprise polymerizing at least one monomer (preferably, at least one fluorine-containing monomer) in the presence of at least one polymerization initiator and at least one fluorinated ether according to the present disclosure.

Objects and advantages of this disclosure are further illustrated by the following non-limiting examples, but the particular materials and amounts thereof recited in these examples, as well as other conditions and, details, should not be construed to unduly limit this disclosure.

EXAMPLES

Unless otherwise noted, all parts, percentages, ratios, etc. in the Examples and the rest of the specification are by weight. In the following examples: the abbreviation "GC" refers to gas chromatography using a flame ionization detector (uncorrected for response factors); "IR" refers to infrared spectroscopy, "GC/MS" refers to gas chromatography—mass spectroscopy; "NMR" (e.g., $^1$H, $^{19}$F, $^{13}$C) refers to nuclear magnetic resonance spectroscopy; "mL" refers to milliliters, "mol" refers to moles; and "g" refers to grams.

Preparation of 2,2,3,4,4,4-hexafluorobutyl 1,1,2,2,3,3,4,4,4-nonafluorobutane-1-sulfonate 2,2,3,4,4,4-hexafluorobutan-1-ol (202 g, 1.1 mol, obtained from Sinochem Corp., Beijing, China), 1,1,2,2,3,3,4,4,4-nonafluorobutane-1-sulfonyl fluoride (332 g, 1.1 mol, obtained from 3M Company of Saint Paul, Minn.) and water (300 g) were combined in a 3-L, 3-necked round bottom flask. The flask was equipped with a magnetic stirrer, cold water condenser, thermocouple and a 250-mL addition funnel. Aqueous potassium hydroxide (149.3 g, 45 weight percent, 1.22 equivalents) was added dropwise via an addition funnel at such a rate that the temperature did not exceed 35° C. Once the addition of the base was complete the mixture was stirred for 16 hours at room temperature. The precipitated salts were then filtered from the mixture and the lower liquid fluorochemical product phase was separated from the upper aqueous phase. Unreacted 2,2,3,4,4,4-hexafluorobutan-1-ol and 1,1,2,2,3,3,4,4,4-nonafluorobutane-1-sulfonyl fluoride were removed by atmospheric distillation.

Preparation of 2,2,3,3-tetrafluoropropyl 1,1,2,2,3,3,4,4,4-nonafluorobutane-1-sulfonate 2,2,3,3-tetrafluoropropan-1-ol (202 g, 1.52 mol, obtained from Sinochem Corp.), 1,1,2,2,3,3,4,4,4-nonafluorobutane-1-sulfonyl fluoride (465 g, 1.52 mol, obtained from 3M Company) and water (500 g) were combined in a 3-liter, 3-necked round bottom flask. The flask was equipped with a magnetic stirrer, cold water condenser, thermocouple and an addition funnel. Aqueous potassium hydroxide (45 percent by weight, 211.5 g, 1.7 mol, obtained from Aldrich Chemical Co., Milwaukee, Wis.) was added dropwise via the addition funnel at such a rate that the temperature did not exceed 35° C. Once the addition of the potassium hydroxide was complete, the mixture was stirred for 16 hours at room temperature. Precipitated salts were then filtered from the mixture and the lower liquid fluorochemical product phase was separated from the upper aqueous phase. Unreacted 2,2,3,3-tetrafluoropropan-1-ol and 1,1,2,2,3,3,4,4,4-nonafluorobutane-1-sulfonyl fluoride were removed from the liquid fluorochemical product phase by atmospheric distillation.

Preparation of 2,2,3,3,4,4,4-heptafluorobutyl 1,1,2,2,3,3,4,4,4-nonafluorobutane-1-sulfonate 2,2,3,3,4,4,4-heptafluorobutan-1-ol (200 g, 1.0 mol, obtained from 3M Company) and 1,1,2,2,3,3,4,4,4-nonafluorobutane-1-sulfonyl fluoride (300 g, 1.0 mol, obtained from 3M Company) were combined in a 1-liter, 3-necked round bottom flask. The flask was equipped with an overhead mechanical stirrer, cold water condenser, thermocouple and an addition funnel. Aqueous potassium hydroxide (45 percent by weight in water, 154 g, 1.05 mol) was added dropwise via the addition funnel at such a rate that the temperature did not exceed 35° C. Once the addition of the potassium hydroxide was complete, the mixture was stirred for 16 hours at room temperature. Precipitated salts were then filtered from the mixture and the lower liquid fluorochemical product phase was separated from the upper aqueous phase and washed once with water to give 350 g crude product. The product was distilled at atmospheric pressure and the distillation cut boiling from 140-150° C. used without further purification (96.3 percent purity by GC).

Preparation of 2,2,3,3-tetrafluoropropyl trifluoromethanesulfonate 2,2,3,3-tetrafluoropropan-1-ol (244.3 g, 1.85 mol, obtained from Sinochem Corp.), triethylamine (187.2 g, 1.85 mol, obtained from Aldrich Chemical Co.) and 500 mL of chloroform were combined in a 2-liter Parr pressure reactor and sealed. The reactor temperature was set to −10° C. Trifluoromethanesulfonyl fluoride (281.33 g, 1.85 mol, obtained from 3M Company) was added at such a rate that the temperature did not exceed −5° C. Once the addition was complete, the mix was held at −10° C. for 45 minutes. The reaction mix was then emptied and washed with 2×500 mL portions of water and 1×250 mL portion of 1N HCl. GC analysis of the reaction mixture indicated a 97 percent conversion to the product. The chloroform solvent was removed by rotary evaporation. The product was dried over anhydrous magnesium sulfate which was then filtered from the product.

Example 1

Preparation of 4-(2',2',3',4',4',4'-hexafluorobutoxy)-1, 1,1,2,3,3-hexafluorobutane, $CF_3$ $CFHCF_2CH_2OCH_2CF_2CFHCF_3$ 2,2,3,4,4,4-hexafluorobutan-1-ol (61.3 g, 0.337 mol, obtained from Sinochem Corp.), 2,2,3,4,4,4-hexafluorobutyl 1,1,2,2,3,3,4,4,4-nonafluorobutane-1-sulfonate (156.4 g, 0.337 mol), potassium carbonate (46.5 g, 0.337 mol), tri-n-butylamine (0.75 g, 0.004 mol) and 150 mL of acetone were combined in a 600-mL Parr pressure reactor. The mix was heated to 75° C. with vigorous stirring for 18 hours. The mix was then emptied and the solids were filtered from the product. The liquid product was washed twice with 100 mL portions of water. Alkylation yield based on GC analysis (uncorrected for response factors) was 60 percent. A clear phase resulted that was then purified by fractional distillation using a concentric tube column resulting in 4-(2,2,3,4,4,4-hexafluorobutoxy)-1,1,1,2,3,3-hexafluorobutane, boiling point=150° C. Purity of this distilled fraction was 98 percent based on GC analysis (uncorrected for response factors). GC/MS analysis was consistent with the assigned structure.

Example 2

Preparation of 5-(2',2',3',4',4',4'-hexafluorobutoxy)-1,1,2,2,3,3,4,4-octafluoropentane, $H(CF_2CF_2)_2CH_2OCH_2CF_2CFHCF_3$ 2,2,3,3,4,4,5,5-Octafluoropentan-1-ol (78.2 g, 0.337 mol, obtained from Sinochem Corp.), 2,2,3,4,4,4-hexafluorobutyl 1,1,2,2,3,3,4,4,4-nonafluorobutane-1-sulfonate (156.4 g, 0.337 mol), potassium carbonate (46.5 g, 0.337 mol), tri-n-butylamine (0.75 g, 0.004 mol) and 150 mL acetone were combined in a 600 mL Parr pressure reactor. The mix was heated to 75° C. with stirring for 18 hours. The salts were filtered from the product. The product was washed with 2×100 mL portions of water to remove extra salts. A resultant fluorochemical product phase was separated and dried over anhydrous magnesium sulfate. 5-(2,2,3,4,4,4-Hexafluorobutoxy)-1,1,2,2,3,3,4,4-octafluoropentane was then obtained by fractional distillation using a concentric tube column. The main fraction boiled between 176-178° C., and GC/MS analysis was consistent with the assigned structure.

Example 3

Preparation of 5-(2',2',3',3'-tetrafluoropropoxy)-1,1,2,2,3,3,4,4-octafluoropentane, $H(CF_2CF_2)_2CH_2OCH_2CF_2CF_2H$ 2,2,3,3,4,4,5,5-Octafluoropentan-1-ol (424 g, 1.83 mol, obtained from Sinochem Corp.), 2,2,3,3-tetrafluoropropyl 1,1,2,2,3,3,4,4,4-nonafluorobutane-1-sulfonate (760 g, 1.83 mol), potassium carbonate (252 g, 1.83 mol), tetra-n-butylammonium bromide (20 g, 0.06 mol) and 400 g of acetone were combined in a 2-liter Parr pressure reactor. The temperature was set to 75° C. and the mix was stirred for 72 hours. The mix was then emptied and the salts were filtered from the product solution. The product solution was washed twice with 200 mL portions of water to remove additional salts. The lower fluorochemical phase was then dried over anhydrous magnesium sulfate, filtered and then purified by fractionation using a 20-plate Oldershaw distillation column. The main fraction (approximately 98 percent purity as measured by GC, uncorrected for response factors) boiled at a temperature of 170° C. at atmospheric pressure. The structure was consistent with analysis by GC/MS, $^{19}F$ NMR, and $^1H$ NMR.

Example 4

Preparation of 1,1,2,2,3,3,4,4-octafluoro-5-(2',2',3',3',4',4',5',5'-octafluoropentyloxy)pentane, $HCF_2CF_2CF_2CF_2CH_2OCH_2CF_2CF_2CF_2CF_2H$ 2,2,3,3,4,4,5,5-Octafluoropentan-1-ol (22.1 g, 0.097 mol) was added dropwise at 50° C. to a suspension of sodium hydride (2.5 g of 95 percent purity, 0.097 mol) in anhydrous diethylene glycol dimethyl ether (200 g) over a two hour period. At the end of this time, the solution was homogeneous. To this solution was then added $HCF_2CF_2CF_2CF_2CH_2OS(=O)_2CH_2CF_2CF_2CF_2CF_3$ (50 g, 0.097 mol) prepared by reaction of $HCF_2CF_2CF_2CF_2CH_2OH$ with $CF_3CF_2CF_2CF_2SO_2F$ with triethylamine at 0° C. The reaction mixture was then heated to 95° C. for 16 hours and 105° C. for an additional six hours. After the reaction was complete, water (100 milliliters) was added, and the mixture distilled using a Dean-Stark trap to return the water and organic solvent back to the distillation vessel while allowing separation of the lower fluorochemical phase in the trap. A preliminary purification was carried out by distillation of the 30.1 g obtained through a concentric tube distillation column. The distillate (204-207° C.) was found to consist of two main components in a 75/21 mixture (as determined by gas chromatography (GC) uncorrected for response factors)), which were $HCF_2CF_2CF_2CF_2CH_2OS(=O)_2CF_2CF_2CF_2CF_3$ and $HCF_2CF_2CF_2CF_2CH_2OCH_2CF_2CF_2CF_2CF_2H$.

Purification of the ether was effected by treatment of the nonaflate-contaminated mixture with a solution of lithium chloride (25 g) in dimethylformamide (200 mL) at 50° C. Under these specific conditions, the nonaflate was found to react rapidly with the lithium chloride to give $HCF_2CF_2CF_2CF_2CH_2Cl$ and lithium nonaflate. The reaction mixture was poured into water, the lower fluorochemical phase separated and washed twice more with water and the resulting mixture distilled (boiling point: 205° C., 70° C./2 at mm Hg) to give a purity of 91.5 percent as measured by GC, uncorrected for response factors. The assigned structure was consistent with the GC/MS analysis, infrared spectroscopy, $^{19}F$ NMR, $^1H$ NMR, and $^{13}C$ NMR.

Example 5

Preparation of 1-(3'-(2'',2'',3'',3''-tetrafluoropropoxy)-1',2',2'-trifluoropropoxy)-1,1,2,2,3,3,3-heptafluoropropane $CF_3CF_2CF_2OCFHCF_2CH_2OCH_2CF_2CF_2H$ 2,2,3-Trifluoro-3-(perfluoropropoxy)propanol (71.6 g, 0.24 mol, prepared as described in U.S. Pat. Appln. Publ. No. 2007/0051916 A1 (Flynn et al.), Example 1), 2,2,3,3-tetrafluoropropyl 1,1,2,2,3,3,4,4,4-nonafluorobutane-1-sulfonate (119.23 g, 0.288 mol), potassium carbonate (39.7 g, 0.288 mol), tri-n-butylamine (0.75 g, 0.004 mol) and 150 mL of acetone were combined in a 600-mL Parr pressure reactor. The temperature of the reactor was set to 75° C. and the mix was stirred for 24 hours. The mix was then emptied and the salts were filtered from the product solution. The product solution was washed twice with 100 mL portions of water to remove additional salts. The lower phase was then dried over anhydrous magnesium sulfate, filtered and then purified by fractional distillation using a concentric tube column. The main fraction (94 percent purity by GC, uncorrected for response factors) boiled at a temperature of 161-162° C. at atmospheric pressure. The assigned structure was consistent with the GC/MS analysis.

Example 6

Preparation of 4-(2',2',3',4',4',4'-hexafluorobutoxy)-1,1,1,2,3,3-hexafluorobutane, $CF_3CFHCF_2CH_2OCH_2CF_2CFHCF_3$ 2,2,3,4,4,4-Hexafluorobutan-1-ol (50 g, 0.27 mol), 2,2,3,3,4,4,5,5,5-nonafluorobutanesulfonyl fluoride (41.5 g, 0.14 mol, obtained from Sinochem International Corp.), potassium carbonate (38.2 g, 0.27 mol), tetrabutylammonium bromide (1.2 g, 0.004 mol) and 153 g of acetone (solvent) were combined in a 600-mL Parr pressure reactor. The mixture was heated to 75° C. with vigorous stirring for 16 hours. After cooling, the reactor was opened and the contents added to water, the lower phase separated and this lower fluorochemical phase was washed once more with about a five-fold excess of aqueous sodium chloride (approximately 5 percent) solution. GC analysis, uncorrected for response factors, confirmed the presence of $CF_3CFHCF_2CH_2OCH_2CF_2CFHCF_3$ by comparison with the sample prepared in Example 1 (above) in a GC yield of 16 percent.

Example 7

Preparation of 3-(2,2,3,3-tetrafluoropropoxy)-1,1,2,2-tetrafluoropropane, $HCF_2CF_2CH_2OCH_2CF_2CF_2H$

2,2,3,3-Tetrafluoropropan-1-ol (50 g, 0.38 mol), 2,2,3,3-tetrafluoropropyl 1,1,2,2,3,3,4,4,4-nonafluorobutane-1-sulfonate (157 g, 0.38 mol), potassium carbonate (52.3 g, 0.38 mol and 197 g of acetone (solvent) were combined in a 600-mL Parr pressure reactor. After degassing, the reactor was sealed and the mixture was heated to 75° C. with vigorous stirring for 18 hours. After cooling, the reactor was opened and the contents filtered to remove the insoluble salts. The acetone was removed by rotary evaporation. To this residue was then added an excess of water and the product azeotropically distilled using a Dean Stark trap to give after phase separation and water washing 52.7 g crude product. Some of the product ether distilled with the solvent during the rotary evaporation so the distillate was poured into water and the lower fluorochemical phase separated and washed once with water (17.8 g). The yield at this stage based on the combined fluorochemical phases by GC analysis was 52 percent. The product was distilled at atmospheric pressure and the distillation cut from 112-152° C. subsequently treated with LiCl (20 g) in N,N-dimethylformamide (150 mL) at 50° C. as described in Example 4 to remove the residual 2,2,3,3-tetrafluoropropyl 1,1,2,2,3,3,4,4,4-nonafluorobutane-1-sulfonate. The product was then distilled through the concentric tube column to give the product ether, boiling point=134-135° C. in 98.6 percent purity. The structure was consistent with the GC/MS, IR, $^{19}F$ NMR, $^1H$ NMR, and $^{13}C$ NMR.

Example 8

Preparation of 5-(2,2,2-trifluoroethoxy)-1,1,2,2,3,3,4,4-octafluoropentane; $H(CF_2CF_2)_2CH_2OCH_2CF_3$

2,2,3,3,4,4,5,5-Octafluoropentan-1-ol (50 g, 0.215 mol), 2,2,2-trifluoroethyl trifluoromethanesulfonate (50 g, 0.215 mol, obtained from Synquest Labs, Inc., Alachua, Fla.), potassium carbonate (29.7 g, 0.215 mol) and 175 g of acetone (solvent) were combined in a 600-mL Parr pressure reactor. After degassing, the reactor was sealed and the mixture was heated to 75° C. with vigorous stirring for 16 hours. After cooling, the reactor was opened and the contents filtered to remove the insoluble salts. The acetone was removed by rotary evaporation. To this residue was then added an excess of water and the product azeotropically distilled using a Dean Stark trap to give after phase separation and water washing 60.4 g crude product. The yield at this stage by GC analysis was 50 percent. The product was distilled at atmospheric pressure and the distillation cuts greater than 138° C. were combined with the pot and subsequently treated with LiCl (15 g) in N,N-dimethylformamide (250 mL) at 50° C. as described in Example 4 to remove the residual 2,2,2-trifluoroethyl trifluoromethanesulfonate. The product was then distilled through the concentric tube column to give the product ether, boiling point=138-143° C. in 95.9 percent purity. The structure was consistent with GC/MS and $^1H$ NMR analysis.

Example 9

Preparation of 4-(2,2,3,3,4,4,4-heptafluorobutoxy)-1,1,1,2,2,3,3-heptafluorobutane; $C_3F_7CH_2OCH_2C_3F_7$

2,2,3,3,4,4,4-Heptafluorobutan-1-ol (50 g, 0.25 mol, obtained from 3M Company), 2,2,3,3,4,4,4-heptafluorobutyl 1,1,2,2,3,3,4,4,4-nonafluorobutane-1-sulfonate (120.5 g, 0.25 mol, prepared as described above), potassium carbonate (34.5 g, 0.25 mol) and 175 g of acetone (solvent) were combined in a 600-mL Parr pressure reactor. After degassing, the reactor was sealed and the mixture was heated to 75° C. with vigorous stirring for 112 hours. After cooling, the reactor was opened and the contents filtered to remove the insoluble salts. The acetone was removed by rotary evaporation. Some of the product ether distilled with the solvent during the rotary evaporation so the distillate was poured into water and the lower fluorochemical phase separated and added to the rotary evaporation residue. To this residue was then added approximately 250 mL water and the product azeotropically distilled using a Dean-Stark trap to give after phase separation and water washing 62 g crude product. The yield at this stage by GC analysis was 11 percent. The product was treated with LiCl (15 g) in N,N-dimethylformamide (250 mL) at 50° C. as described in Example 4 to remove the residual nonafluorobutane-1-sulfonate. The product was then distilled to a purity of 78 percent. GC/MS and $^1H$ NMR were consistent with the assigned structure

Example 10

Preparation of 3-(2,2,3,3-tetrafluoropropoxy)-1,1,2,2-tetrafluoropropane, $HCF_2CF_2CH_2OCH_2CF_2CF_2H$ using 2,2,3,3-tetrafluoropropyl trifluoromethanesulfonate

2,2,3,3-tetrafluoropropyl trifluoromethanesulfonate (44 g, 0.166 mol), 2,2,3,3-tetrafluoropropan-1-ol (22 g, 0.166 mol, obtained from), potassium carbonate (23 g, 0.166 mol), tetrabutylammonium bromide (0.53 g 0.00166 mol) and acetone (200 mL) were combined in a 600-mL Parr reactor. The reactor was sealed and heated to 75° C. for 24 hours. The reaction mix was then emptied from the reactor and the salts were filtered from the liquid. GC analysis indicated that 66 percent of the fluoroalcohol was converted to the symmetrical ether product based on known reference samples that were prepared as in Example 7.

Example 11

Preparation of $C_3F_7CH_2OCH_2C_2F_4CH_2OCH_2C_3F_7$

2,2,3,3-Tetrafluorobutane-1,4-diol ($HOCH_2C_2F_4CH_2OH$, 20 g, 0.123 mol, obtained from 3M Company), 2,2,3,3,4,4,4-heptafluorobutyl-1,1,2,2,3,3,4,4,4-nonafluorobutane-1-sulfonate ($C_3F_7CH_2OSO_2C_4F_9$, 119 g, 0.247 mol, prepared as described above), potassium carbonate (34.1 g, 0.247 mol) and 245 g of acetone (solvent) were combined in a 600-mL Parr pressure reactor. After degassing, the reactor was sealed and the mixture was heated to 75° C. with vigorous stirring for 112 hours. After cooling, the reactor was opened and the contents filtered to remove the insoluble salts. The acetone was removed by rotary evaporation. To this residue was then added an excess of water, and the product azeotropically distilled using a Dean-Stark trap to give after phase separation and water washing 57.2 g crude product. GC/MS analysis was consistent with the presence of the expected product $C_3F_7CH_2OCH_2C_2F_4CH_2OCH_2C_3F_7$ as a component in a more complex mixture (about 8.4 percent yield by GC).

Example 12

Preparation of $(CF_3)_2NC_2F_4CH_2OCH_2C_4F_8H$

3-[Bis(trifluoromethyl)amino]-2,2,3,3-tetrafluoro-propan-1-ol ($(CF_3)_2NC_2F_4CH_2OH$, 25 g, 0.088 mol, 3M Company, Saint Paul, Minn.), $HCF_2CF_2CF_2CF_2CH_2OS(=O)_2CF_2CF_2CF_2CF_3$ (45.4 g, 0.088 mol) prepared as described in Example 4, potassium carbonate (12.2 g, 0.088 mol) and 175 g of acetone (solvent) were combined in a 600-mL Parr pressure reactor. After degassing, the reactor was sealed and the mixture was heated to 75° C. with vigorous stirring for 64 hours. After cooling, the reactor was opened and the contents filtered to remove the insoluble salts. The acetone was removed by rotary evaporation. To this residue was then added an excess of water and the product azeotropically distilled using a Dean-Stark trap to give after phase separation and water washing 30.3 g crude product. GC/MS analysis was consistent with the presence of the expected product $(CF_3)_2NC_2F_4CH_2OCH_2C_4F_8H$ as a component in a more complex mixture (about 6 percent yield by GC). The mixture was distilled to a purity of about 35 percent of the ether, for which the $^1$H-NMR was consistent with the structure.

All patents and publications referred to herein are hereby incorporated by reference in their entirety. Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A method of making a fluorinated ether, the method comprising:
   combining in a polar aprotic solvent:
      a fluorinated alcohol represented by the formula $X-R_f^1-CH_2OH$ wherein
         $R_f^1$ is selected from the group consisting of derivatives of perfluorinated alkylene groups having from 1 to 10 carbon atoms wherein one or more carbon atoms are replaced by catenated heteroatoms, and derivatives of partially fluorinated alkylene groups having from 1 to 10 carbon atoms wherein one or more carbon atoms are replaced by catenated heteroatoms, wherein if $R_f^1$ contains at least two carbon atoms, then $R_f^1$ contains at most two hydrogen atoms; and
         X represents H, F, or an $HOCH_2-$ group;

a fluorinated sulfonate ester represented by the formula $R_f^2CH_2OS(=O)_2R_f^3$ wherein
         $R_f^2$ is selected from the group consisting of perfluorinated alkyl groups having from 1 to 10 carbon atoms and partially fluorinated alkyl groups having from 1 to 10 carbon atoms, and derivatives thereof wherein one or more carbon atoms are replaced by catenated heteroatoms, and wherein if $R_f^2$ contains at least two carbon atoms then $R_f^2$ contains at most three hydrogen atoms; and $R_f^3$ is selected from the group consisting of perfluorinated alkyl groups having from 1 to 4 carbon atoms; and
      base; and
   obtaining at least one fluorinated ether represented by the formula $Y-R_f^1-CH_2OCH_2R_f^2$ wherein Y represents H, F, or an $R_f^2CH_2OCH_2-$ group.

2. The method of claim 1, wherein at least one of $R_f^1$ or $R_f^2$ is perfluorinated and has from 1 to 10 carbon atoms.

3. The method of claim 2, wherein at least one of $R_f^1$ or $R_f^2$ contains a secondary carbon atom having one hydrogen atom and one fluorine atom bonded thereto.

4. The method of claim 1, wherein at least one of $R_f^1$ or $R_f^2$ has 3 to 8 carbon atoms.

5. A method of making a fluorinated ether, the method comprising:
   combining in a polar aprotic solvent:
      a fluorinated alcohol represented by the formula $Z-R_f^1-CH_2OH$ wherein:
         Z represents H or F;
         $R_f^1$ is selected from the group consisting of derivatives of perfluorinated alkylene groups having from 1 to 10 carbon atoms wherein one or more carbon atoms are replaced by catenated heteroatoms, and derivatives of partially fluorinated alkylene groups having from 1 to 10 carbon atoms wherein one or more carbon atoms are replaced by catenated heteroatoms, wherein if $R_f^1$ contains at least two carbon atoms, then $R_f^1$ contains at most two hydrogen atoms; and
      a sulfonyl fluoride represented by the formula $R_f^3S(=O)_2F$ wherein $R_f^3$ is selected from the group consisting of perfluorinated alkyl groups having from 1 to 4 carbon atoms; and
      base; and
   obtaining a fluorinated ether represented by the formula $Z-R_f^1-CH_2OCH_2-R_f^1-Z.$

* * * * *

UNITED STATES PATENT AND TRADEMARK OFFICE
CERTIFICATE OF CORRECTION

PATENT NO. : 7,988,877 B2  
APPLICATION NO. : 12/263661  
DATED : August 2, 2011  
INVENTOR(S) : Richard Mark Flynn It is certified that error appears in the above-identified patent and that said Letters Patent is hereby corrected as shown below:

In the claims:

Column 14
Line 44, in Claim 5, delete "$R_f^1$contains" and insert -- $R_f^1$ contains --, therefor.

Column 14
Line 54, in Claim 5, delete "Z—$R_f^1$—CH$_2$OCH$_2$—$R_f^1$—Z." and insert
-- Z—$R_f^1$—CH$_2$OCH$_2$—$R_f^1$—Z. --, therefor.

Signed and Sealed this
Twenty-fifth Day of October, 2011

David J. Kappos
*Director of the United States Patent and Trademark Office*